United States Patent
Liao et al.

(10) Patent No.: US 9,951,036 B2
(45) Date of Patent: Apr. 24, 2018

(54) METHOD FOR PREPARING CANAGLIFLOZIN INTERMEDIATE 2-(2-METHYL-5-BROMOBENZYL)-5-(4-FLUOROPHENYL)THIOPHENE

(71) Applicants: ZHEJIANG HUAHAI PHARMACEUTICAL CO., LTD., Taizhou, Zhejiang (CN); SHANGHAI SYNCORES TECHNOLOGIES INC. LTD., Shanghai (CN)

(72) Inventors: Wenjing Liao, Shanghai (CN); Xiaowen Guo, Shanghai (CN); Luning Huang, Shanghai (CN); Eric Gu, Shanghai (CN)

(73) Assignees: SHANGHAI SYNCORES TECHNOLOGIES INC. LTD., Shanghai (CN); ZHEJIANG HUAHAI PHARMACEUTICAL CO., LTD, Zhejiang (CN)

( * ) Notice: Subject to any disclaimer, the term of this patent is extended or adjusted under 35 U.S.C. 154(b) by 0 days.

(21) Appl. No.: 15/308,456

(22) PCT Filed: Jun. 19, 2015

(86) PCT No.: PCT/CN2015/081952
§ 371 (c)(1),
(2) Date: Nov. 2, 2016

(87) PCT Pub. No.: WO2016/008351
PCT Pub. Date: Jan. 21, 2016

(65) Prior Publication Data
US 2017/0044129 A1    Feb. 16, 2017

(30) Foreign Application Priority Data
Jul. 18, 2014   (CN) ............................ 201410344963

(51) Int. Cl.
*C07D 333/12*    (2006.01)
(52) U.S. Cl.
CPC .................................. *C07D 333/12* (2013.01)
(58) Field of Classification Search
CPC ................................................... C07D 333/12
USPC ....................................................... 549/80
See application file for complete search history.

(56) References Cited

U.S. PATENT DOCUMENTS

2006/0160828 A1   7/2006   Malamas et al.

FOREIGN PATENT DOCUMENTS

| CN | 102115468 A | 7/2011 |
| CN | 103649033 A | 3/2014 |
| WO | 2012/160218 A1 | 11/2012 |

OTHER PUBLICATIONS

Alfar Aesar,L13961, pp. 1-2.*
Acros Organics, Aluminium Hydrides and Borohydrides, pp. 1-40.*
Abdelsamie, A.S., et al., "Inhibition of 17β-HSD1: SAR of Bicyclic Substituted Hydroxyphenylmethanones and Discovery of New Potent Inhibitors with Thioether Linker", European Journal of Medicinal Chemistry, vol. 82, Jun. 3, 2014, pp. 394-406, especially p. 399, procedure 2 and p. 400, procedure 3.
Nomura, S. et al., "Discovery of Canagliflozin, a Novel C-Glucoside with Thiophene Ring, as Sodium-Dependent Glucose Cotransporter 2 Inhibitor for the Treatment of Type 2 Diabetes Mellitus", Journal of Medicinal Chemistry, vol. 53, No. 1; Aug. 6, 2010, pp. 6355-6360, especially p. 6356, procedure 2 and p. 6358, right column, last paragraph.
Doyle et al., Silane Reductions in Acidic Media. VIII. Boron Trifluoride Catalyzed Organosilane Reductions. Selectivity and Mechanism. Journal of Organometallic Chemistry. 1976;117:129-140.
Hulshof et al., Synthesis and Structure—Activity Relationship of the First Nonpeptidergic Inverse Agonists for the Human Cytomegalovirus Encoded Chemokine Receptor US28. J Med Chem. 2005; 48:6461-6471.
Supplementary European Search Report for Application No. 15822421.2, dated Dec. 1, 2017. 8 pages.

* cited by examiner

*Primary Examiner* — Taofiq A Solola
(74) *Attorney, Agent, or Firm* — McCarter & English, LLP; Steven G. Davis; Wei Song

(57) ABSTRACT

Provide in the present invention is a method for preparing canagliflozin intermediate 2-(2-methyl-5-bromobenzyl)-5-(4-fluorophenyl)thiophene. The method comprises a compound, shown as formula (II), of (5-bromo-2-methylphenyl)[5-(p-fluorophenyl)thiophene-2-yl]ketone being reduced under the action of a directly used borane solution or borane locally produced by reacting alkali metal borohydride with a Lewis acid in a suitable solvent and at a suitable temperature, so as to obtain the compound of formula (I) of 2-(2-methyl-5-bromobenzyl)-5-(4-fluorophenyl)thiophene. The preparation method avoids the use of expensive reductive agents and guarantees the complete conversion of raw materials, wherein the post-treatment is simple, the purity of product obtained is high, the reaction yield is high, in the preparation method is simple and convenient, and can easily be used in industry.

6 Claims, No Drawings

METHOD FOR PREPARING CANAGLIFLOZIN INTERMEDIATE 2-(2-METHYL-5-BROMOBENZYL)-5-(4-FLUOROPHENYL)THIOPHENE

CROSS-REFERENCE TO RELATED APPLICATIONS

The present application is a U.S. national stage filing, under 35 U.S.C. § 371(c), of International Application No. PCT/CN2015/081952, filed Jun. 19, 2015, which claims the priority of Chinese Patent Application No. 201410344963.3, titled "METHOD FOR PREPARING CANAGLIFOZIN INTERMEDIATE", filed on Jul. 18, 2014 before SIPO. The entire contents of each of the aforementioned applications are incorporated herein by reference.

FIELD OF THE INVENTION

The present invention relates to the field of synthesizing pharmaceutical intermediates, and in particular to a method for preparing canagliflozin intermediate 2-(2-methyl-5-bromobenzyl)-5-(4-fluorophenyl)thiophene.

BACKGROUND OF THE INVENTION

The structure of Canagliflozin, i.e. (1S)-1,5-dehydro-1-C-[3-[[5-(4-fluorophenyl)-2-thienyl]methyl]-4-methylphenyl]-D-glucitol, is shown as formula III. This medicament is developed by Janssen Pharmaceutical Ltd., a subsidiary of Johnson & Johnson Pharmaceutical Ltd., and approved by FDA on Mar. 29, 2013 as an antihyperglycemic for treating type II diabetes. It is the first sodium-glucose-cotransporter 2 (SGLT2) inhibitor approved by FDA. According to the market share of canagliflozin, the continuously rising number of diabetes patients, and the increasing difficulty of glycemic control for patients, analysts predict that the sales of this medicament will be over 600 million USD till 2016. 2-(2-methyl-5-bromobenzyl)-5-(4-fluorophenyl)thiophene, the structure of which is shown as formula I, is an important intermediate for synthesizing canagliflozin. Thus, in view of the market prospect of canagliflozin, it is very necessary to study the synthesis of 2-(2-methyl-5-bromobenzyl)-5-(4-fluorophenyl)thiophene.

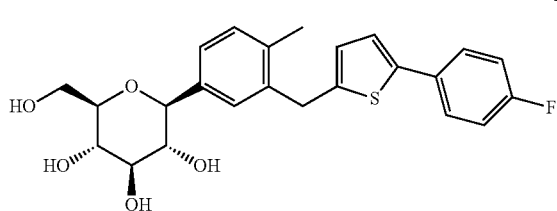

III

Chinese Patent Application CN103214471A reports that 2-(2-methyl-5-bromobenzyl)-5-(4-fluorophenyl)thiophene is obtained by a reduction reaction using (5-bromo-2-methylphenyl)[5-(p-fluorophenyl)thiophene-2-yl]methanone as raw material, under the reaction condition of the raw material being treated with a silicane reagent (triethyl silicane, etc.) in a proper solvent (such as acetonitrile, dichloromethane, etc.) in the presence of an acid (BF$_3$.Et$_2$O, or trifluoroacetic acid, methanesulfonic acid, etc.), or being treated with hydrazine hydrate at high temperature under rare gas atmosphere in a proper solvent (such as ethylene glycol, etc.) in the presence of a base. In one aspect, this method requires silicane reagent, which is expensive, inflammable and has irritating smells; it has low yield of only 78%; and moreover, it requires purification by chromatography, thus the post-treatment is complicated. In another aspect, if hydrazine hydrate is used for the reduction treatment, a rare gas atmosphere is required for performing the method, so that the reaction condition is harsh, which is not suitable for industrial production; in addition, a high temperature of 190° C. is required for performing the method, resulting in high power consumption, and high costs.

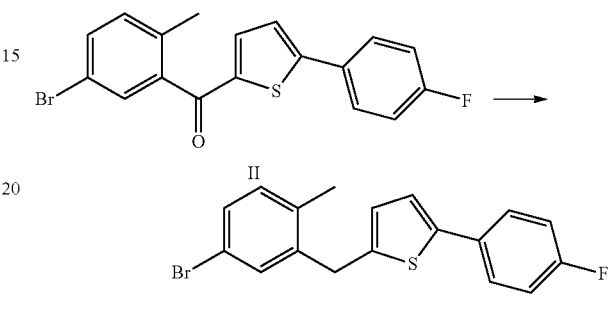

SUMMARY OF THE INVENTION

An object of present invention is to provide a method for preparing canagliflozin intermediate 2-(2-methyl-5-bromobenzyl)-5-(4-fluorophenyl)thiophene. In this method, 2-(2-methyl-5-bromobenzyl)-5-(4-fluorophenyl)thiophene is obtained by reducing (5-bromo-2-methylphenyl)[5-(p-fluorophenyl)thiophene-2-yl]methanone under the effect of a borane. This preparation method has the advantages of complete conversion, cheap reductive agent, simple post-treatment, high purity of the obtained product, high reaction yield and simple preparation method, and is easy for industrial application. The object of present invention is achieved by the following technical solution.

The present invention provides a method for preparing a compound of 2-(2-methyl-5-bromobenzyl)-5-(4-fluorophenyl)thiophene shown as formula (I), comprising the steps of: subjecting a compound of (5-bromo-2-methylphenyl)[5-(p-fluorophenyl)thiophene-2-yl]methanone shown as formula (II) to a reduction reaction under the effect of a borane to obtain the compound of formula (I).

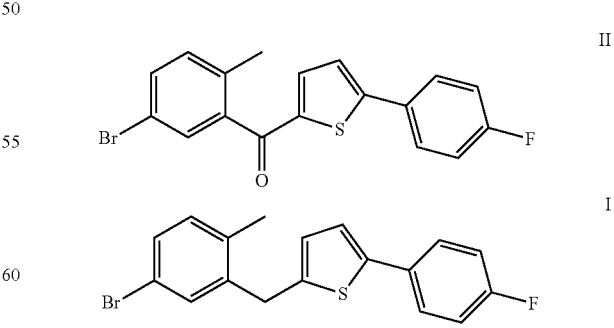

In the present invention, the raw material of (5-bromo-2-methylphenyl)[5-(p-fluorophenyl)thiophene-2-yl]methanone can be synthesized as described in Example 1 of Chinese Patent Application CN101801371A.

According to the method for preparing 2-(2-methyl-5-bromobenzyl)-5-(4-fluorophenyl)thiophene of the present invention, as the borane, a borane solution can be used directly or a borane produced in situ can be used. In a preferred embodiment, the borane produced in situ can be produced by the reaction of an alkali metal borohydride and a Lewis acid. In a preferred embodiment, the alkali metal is selected from sodium or potassium. In a preferred embodiment, the alkali metal borohydride is selected from sodium borohydride, potassium borohydride, sodium triacetoxyborohydride and sodium cyanoborohydride, etc. In a preferred embodiment, the Lewis acid is selected from aluminium trichloride, trifluoroacetic acid or boron trifluoride diethyl etherate solution.

According to the method for preparing 2-(2-methyl-5-bromobenzyl)-5-(4-fluorophenyl)thiophene of the present invention, the reduction reaction is performed in an inert solvent. In a preferred embodiment, the inert solvent is preferably selected from ethers or haloalkanes. In a preferred embodiment, the ether solvent is selected from tetrahydrofuran or dimethyltetrahydrofuran. In a preferred embodiment, the haloalkane solvent is selected from dichloromethane, trichloromethane or 1,2-dichloroethane.

According to the method for preparing 2-(2-methyl-5-bromobenzyl)-5-(4-fluorophenyl)thiophene of the present invention, the reaction temperature is −20 to 85° C., preferably −10 to 70° C.

The method for preparing 2-(2-methyl-5-bromobenzyl)-5-(4-fluorophenyl)thiophene of the present invention has the following advantages, for example: (1) the used reductive agent is cheap, safer in process, and environmentally friendly; (2) the yield of product remarkably increases, up to 90% and above, even to 97.7%; (3) purification by chromatography is not required, and only extraction with organic solvent and concentration are needed, thus the post-treatment is simple; (4) a rare gas atmosphere is not required for performing the reduction reaction, which is beneficial for industrial production; and (5) a high temperature is not required for performing the reduction reaction, thereby saving energy and reducing production cost.

DETAILED DESCRIPTION OF THE INVENTION

The present invention will be further illustrated by following examples. It should be noted that the examples of the present invention are provided only for illustrating the present invention without, however, limiting the present invention.

EXAMPLE 1

10 g (5-bromo-2-methylphenyl)[5-(p-fluorophenyl)thiophene-2-yl]methanone was weighed and dissolved in 100 ml tetrahydrofuran, and 4 ml of 1 M borane-tetrahydrofuran complex was added. The system was heated to 50 to 55° C. and reacted for 12 hours. After the complete reaction of raw materials, 20 ml water was added. The mixture was extracted with 50 ml dichlomomethane, and then the extract was concentrated to give 9.5 g of 2-(2-methyl-5-bromobenzyl)-5-(4-fluorophenyl)thiophene, with a purity of 99.0% and in a yield of 97.7%.

$^1$HNMR (DMSO-d6) δ 2.25 (3H, s), 4.15 (2H, s, Ph-CH$_2$-thiophene), 6.85 (1H, d, J=3.5 Hz, thiophene), 7.17 (1H, d, J=8.0 Hz), 7.21 (2H, quasi-t), 7.31 (1H, d, J=3.5 Hz, thiophene), 7.36 (1H, dd, J=8.0, 1.9 Hz), 7.44 (1H, d, J=1.9 Hz), 7.60 (2H, m).

Anal. Calcd. for C$_{18}$H$_{14}$BrFS: C, 59.84; H, 3.91; Br, 22.12; F, 5.26; S, 8.87. Found: C, 59.89; H, 3.86; Br, 21.93; F, 5.17; S, 8.85.

EXAMPLE 2

10 g (5-bromo-2-methylphenyl)[5-(p-fluorophenyl)thiophene-2-yl]methanone was weighed and dissolved in 100 ml tetrahydrofuran, 1.5 g sodium borohydride and 7.1 g anhydrous aluminium chloride were added. The system was heated to 50 to 55° C. and reacted for 12 hours. After the complete reaction of raw materials, 20 ml water was added. The mixture was extracted with 100 ml ethyl acetate, and then the extract was concentrated to give 9.4 g of 2-(2-methyl-5-bromobenzyl)-5-(4-fluorophenyl)thiophene, with a purity of 98.5% and in a yield of 96.1%.

EXAMPLE 3

20 g (5-bromo-2-methylphenyl)[5-(p-fluorophenyl)thiophene-2-yl]methanone was weighed and dissolved in 200 ml tetrahydrofuran, 4.4 g potassium borohydride and 14.2 g anhydrous aluminium chloride were added. The system was heated to 50 to 55° C. and reacted for 12 hours. After the complete reaction of raw materials, 40 ml water was added. The mixture was extracted with 200 ml ethyl acetate, and then the extract was concentrated to give 18.4 g of 2-(2-methyl-5-bromobenzyl)-5-(4-fluorophenyl)thiophene, with a purity of 98.6% and in a yield of 94.2%.

EXAMPLE 4

30 g (5-bromo-2-methylphenyl)[5-(p-fluorophenyl)thiophene-2-yl]methanone was weighed and dissolved in 300 ml tetrahydrofuran, 9.0 g sodium borohydride and 30 ml of 1M boron trifluoride diethyl etherate complex were added. The system was heated to 60 to 70° C. and reacted for 12 hours. After the complete reaction of raw materials, 60 ml water was added. The mixture was extracted with 300 ml ethyl acetate, and then the extract was concentrated to give 28.2 g of 2-(2-methyl-5-bromobenzyl)-5-(4-fluorophenyl)thiophene, with a purity of 97.9% and in a yield of 95.6%.

EXAMPLE 5

10 g (5-bromo-2-methylphenyl)[5-(p-fluorophenyl)thiophene-2-yl]methanone was weighed and dissolved in 100 ml dichloromethane, 1.5 g sodium borohydride and 7.3 g trifluoroacetic acid were added. The system was heated to 40 to 45° C. and reacted for 20 hours. After the complete reaction of raw materials, 20 ml water was added. The mixture was extracted with 100 ml dichloromethane, and then the extract was concentrated to give 9.2 g of 2-(2-methyl-5-bromobenzyl)-5-(4-fluorophenyl)thiophene, with a purity of 98.5% and in a yield of 94.1%.

EXAMPLE 6

25 g (5-bromo-2-methylphenyl)[5-(p-fluorophenyl)thiophene-2-yl]methanone was weighed and dissolved in 250 ml tetrahydrofuran, 11.0 g potassium borohydride and 36.5 g trifluoroacetic acid were added. The system was heated to 40 to 45° C. and reacted for 22 hours. After the complete reaction of raw materials, 50 ml water was added. The mixture was extracted twice with 250 ml ethyl acetate, and then the extract was concentrated to give 22.75 g of 2-(2- methyl-5-bromobenzyl)-5-(4-fluorophenyl)thiophene, with a purity of 97.8% and in a yield of 92.4%.

EXAMPLE 7

10 g (5-bromo-2-methylphenyl)[5-(p-fluorophenyl)thiophene-2-yl]methanone was weighed and dissolved in 100 ml tetrahydrofuran, 10.5 g sodium triacetoxyborohydride and 8 ml of 1 M borane-tetrahydrofuran complex were added. The system was heated to 60 to 70° C. and reacted for 28 hours. After the complete reaction of raw materials, 20 ml water was added. The mixture was extracted twice with 100 ml ethyl acetate, and then the extract was concentrated to give 9.0 g of 2-(2-methyl-5-bromobenzyl)-5-(4-fluorophenyl)thiophene, with a purity of 96.8% and in a yield of 90.5%.

EXAMPLE 8

15 g (5-bromo-2-methylphenyl)[5-(p-fluorophenyl)thiophene-2-yl]methanone was weighed and dissolved in 150 ml tetrahydrofuran, and 30 ml of 1 M borane-tetrahydrofuran complex was added. The system was reacted at −20° C. to −10° C. for 48 hours. After the complete reaction of raw materials, 30 ml water was added. The mixture was extracted with 100 ml dichloromethane, and then the extract was concentrated to give 14.25 g of 2-(2-methyl-5-bromobenzyl)-5-(4-fluorophenyl)thiophene, with a purity of 98.9% and in a yield of 97.7%.

EXAMPLE 9

10 g (5-bromo-2-methylphenyl)[5-(p-fluorophenyl)thiophene-2-yl]methanone was weighed and dissolved in 100 ml tetrahydrofuran, 3.0 g sodium borohydride and 14.2 g anhydrous aluminium chloride were added. The system was reacted at 0 to 10° C. for 24 hours. After the complete reaction of raw materials, 20 ml water was added. The mixture was extracted with 100 ml ethyl acetate, and then the extract was concentrated to give 9.2 g of 2-(2-methyl-5-bromobenzyl)-5-(4-fluorophenyl)thiophene, with a purity of 98.0% and in a yield of 93.6%.

EXAMPLE 10

25 g (5-bromo-2-methylphenyl)[5-(p-fluorophenyl)thiophene-2-yl]methanone was weighed and dissolved in 250 ml 1,2-dichloroethane, 11.0 g potassium borohydride and 36.5 g trifluoroacetic acid were added. The system was heated to 80 to 85° C. and reacted for 26 hours. After the complete reaction of raw materials, 50 ml water was added. The mixture was extracted twice with 250 ml 1,2-dichloroethane, and then the extract was concentrated to give 22.35 g of 2-(2-methyl-5-bromobenzyl)-5-(4-fluorophenyl)thiophene, with a purity of 98.1% and in a yield of 91.1%.

It can be seen from the examples above that, when compared with prior art, the method according to the invention has the following advantages: (1) the method uses a borane solution directly or a borane produced in situ as reductive agent, which is cheap, safer in process, and environmentally friendly; (2) by using the method of the present invention, the yield of obtained products increases remarkably, up to 90% and above, even to 97.7%; (3) by using the method of the present invention, purification by chromatography is not required, and only extraction with organic solvent and concentration are required, thus the post-treatment is simple; (4) in accordance with the method of the present invention, a rare gas atmosphere is not required for performing the reduction reaction, which is beneficial for industrial production; (5) in accordance with the method of the present invention, a high temperature is not required for performing the reduction reaction, thereby saving energy and reducing production cost; (6) in addition, the applicants also discover that, compared with using a borane produced in situ, the obtained products are better in both purity and yield when using borane solution directly.

The method for preparing 2-(2-methyl-5-bromobenzyl)-5-(4-fluorophenyl)thiophene provided by the present invention has been described by the examples. Change or appropriate modification or the combination thereof can obviously be made to the method for preparing 2-(2-methyl-5-bromobenzyl)-5-(4-fluorophenyl)thiophene by those skilled in art without departing from the content, spirit and scope of the present invention, to achieve the object of the present invention. It should be particularly noted that, all the similar replacements and changes are obvious to a skilled in the art, and they are all deemed to be within the spirit, scope and content of the present invention.

The invention claimed is:

1. A method for preparing a compound of 2-(2-methyl-5-bromobenzyl)-5-(4-fluorophenyl)thiophene shown as formula I, comprising the steps of:
   subjecting a compound of (5-bromo-2-methylphenyl)[5-(p-fluorophenyl)thiophene-2-yl]methanone shown as formula II

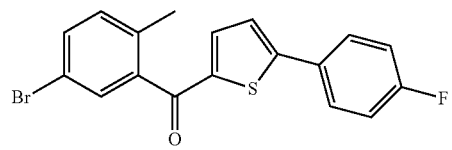

to a reduction reaction under the effect of a borane to obtain the compound of formula I,

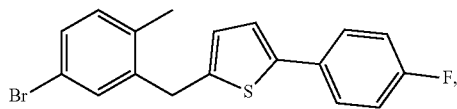

wherein the reduction reaction is performed in an inert solvent selected from ethers or haloalkanes, and wherein the ether is selected from tetrahydrofuran or dimethyltetrahydrofuran, and the haloalkane is selected from dichloromethane, trichloromethane, or 1,2-dichloromethane.

2. The method according to claim 1, characterized in that, as the borane, a borane solution can be used directly or a borane produced in situ can be used.

3. The method according to claim 1, characterized in that, the reduction reaction is performed at a temperature of −20 to 85 ° C.

4. The method according to claim 2, characterized in that, the borane produced in situ is obtained by the reaction of an alkali metal borohydride and a Lewis acid, wherein the alkali metal is selected from sodium or potassium.

5. The method according to claim 4, characterized in that, the alkali metal borohydride is selected from sodium borohydride, potassium borohydride, sodium triacetoxyborohydride or sodium cyanoborohydride.

6. The method according to claim 4, characterized in that, the Lewis acid is selected from aluminium trichloride, trifluoroacetic acid or boron trifluoride diethyl etherate solution.

* * * * *